United States Patent [19]
Haraguchi et al.

[11] Patent Number: 6,008,256
[45] Date of Patent: Dec. 28, 1999

[54] COMPOSITION FOR LOCAL ANESTHESIA

[75] Inventors: Mitsuhiro Haraguchi; Kazuhiro Ono; Takashi Osada; Yukio Suzuki, all of Tokyo, Japan

[73] Assignee: Showa Yakuhin Kako Co., Ltd., Tokyo, Japan

[21] Appl. No.: 09/029,659

[22] PCT Filed: Aug. 27, 1996

[86] PCT No.: PCT/JP96/02395

§ 371 Date: Feb. 27, 1998

§ 102(e) Date: Feb. 27, 1998

[87] PCT Pub. No.: WO97/07794

PCT Pub. Date: Mar. 16, 1997

[30] Foreign Application Priority Data

Aug. 28, 1995 [JP] Japan ..... 7-218468
Mar. 7, 1996 [JP] Japan ..... 8-049770

[51] Int. Cl.⁶ ..... A61K 31/165; A61K 47/12
[52] U.S. Cl. ..... 514/626; 514/817; 514/818; 514/970
[58] Field of Search ..... 514/626, 625, 514/630, 817, 818, 970; 564/194

[56] References Cited

U.S. PATENT DOCUMENTS

| | | | |
|---|---|---|---|
| 5,505,922 | 4/1996 | Thut et al. | 424/677 |
| 5,534,242 | 7/1996 | Henry | 424/45 |
| 5,540,669 | 7/1996 | Sage, Jr. et al. | 604/290 |
| 5,563,153 | 10/1996 | Mueller et al. | 514/305 |

FOREIGN PATENT DOCUMENTS

| | | |
|---|---|---|
| 0622072A2 | 11/1994 | European Pat. Off. . |
| 6-336442 | 12/1994 | Japan . |
| 93/12811 | 7/1993 | WIPO . |
| 96/21460 | 7/1996 | WIPO . |

OTHER PUBLICATIONS

Murakami, Craig S., MD., Buffered Local Anesthetics and Epinephrne Degradation, pp. 192–195.

Zur Prufung der Wirksamkeit von Stabilisatoren bei Epinephrin–Modellosungen, H. Wollmann, et al, Pharmazie 38 (1983), H.1, pp. 37–42.

Drug Development and Industrial Pharmacy, 18 (14), 1549–1566 Stablization of Epinephrine in a Local Anesthetic Injectable Solution Using Reduced Levels of Sodium Metabisulfite and EDTA, B. Grubstein et al.

*Primary Examiner*—Robert H. Harrison
*Attorney, Agent, or Firm*—Birch, Stewart, Kolasch & Birch, LLP

[57] ABSTRACT

A composition for local anesthesia which comprises (A) lidocaine, (B) a catecholamine such as epinephrine in an amount of, for example, 1/200,000 (g/ml) based on the volume of the composition, and (C) one or more amino acids such as glycine, glutamic acid, and L-glutamic acid-L-lysine or one or more hydroxycarboxylic acids such as lactic acid, glycolic acid, and citric acid, which has a duration suitable for short-time dental operations such as tooth extraction and excellent storage stability.

15 Claims, No Drawings

COMPOSITION FOR LOCAL ANESTHESIA

This application is the national phase under 35 U.S.C. §371 of prior PCT International Application No., PCT/JP96/02395, which has an International filing date of Aug. 27, 1996, which designated the United States of America, the entire contents of which are hereby incorporated by reference.

TECHNICAL FIELD

The present invention relates to a composition for local anesthesia. More specifically, the present invention relates to a pharmaceutical composition for local anesthesia which has a duration of local anesthetic action suitable for minor dental operations such as tooth extraction and excellent storage stability.

BACKGROUND ART

For operations in the fields of oral surgery and dental treatment, in particular, for tooth extraction and other in dental treatment, anesthetics for local injection (agents for local anesthesia) containing lidocaine (2-diethylamino-N-(2, 6-dimethyl-phenyl)acetamide) as an active ingredient have been used. For example, "Xylocaine® Cartridge for Dental Use" (Fujisawa Pharmaceutical Co., Ltd.) is clinically used. This agent for local anesthesia is a composition for topical administration which contains 20 mg of lidocaine hydrochloride and 0.0125 mg of epinephrine per 1 ml of parenteral solution. The agent is usually used in an amount of 0.3–1.8 ml to carry out infiltration anesthesia or block anesthesia (see, a package insert of the drug).

Agents for local anesthesia are generally formulated with a catecholamine such as epinephrine which has angiotonic effect on local capillary blood vessels to reduce blood flow. The effect of the catecholamine is to decrease bleeding in a filed of operation by lowering blood flow, and to reduce transmigration (diffusion) of an anesthetic agent being an active ingredient into blood and maintain high concentration of the anesthetic agent in the local tissue to achieve a prolonged local anesthetic effect (Collins, V. J., Principles of Anesthesiology, 2nd Ed., Lea and Febiger, Philadelphia, 1976; as a review about agents for dental local anesthesia, see, Dental Outlook, special edition, "Medical practice of tooth extraction," 4. Dental local anesthetics, pp.84–94, 1979).

However, when the aforementioned agent for local anesthesia is used for dental operations such as tooth extraction, which may be completed in a short period of time such as in several to 10 minutes, the local anesthetic effect tends to be maintained longer than required. In a consequence, oral and glossal benumbedness may remain several hours after the operation, and difficulties may arise in eating and drinking. In addition, a catecholamine such as epinephrine constricts blood vessels to decrease blood flow in a tissue and increases local oxygen consumption. For this reason, when vasoconstriction is maintained for longer hours than needed, tissue necrosis and delay of wound healing may possibly be caused. Accordingly, a development of an agent for local anesthesia has been desired which have a duration suitable for short-time operations such as tooth extraction.

A content ratio of a catecholamine added to a local anesthetic is generally recommended to be around 1/50,000–1/200,000 (g/ml) based on the volume (ml) of a local anesthetic agent (see, the above-described "Dental Outlook," special edition, "Medical practice of tooth extraction," p.92, right column), and dental lidocaine preparations which have been clinically used so far contain 1/80,000 (g/ml, 0.0125 mg/ml) of epinephrine. The inventor of the present invention conducted various studies to provide an agent for local anesthesia which has a duration suitable for short-time dental operations such as tooth extraction, and as a result, they found that a necessary and sufficient duration of local anesthetic action for a dental anesthesia can be achieved by adding about 1/200,000 of epinephrine (g/ml, 0.005 mg as a free base per ml).

Catecholamines such as epinephrine and norepinephrine are known to be unstable under neutral or alkaline conditions, and readily oxidized by an oxidizing agent such as oxygen, and colored to give a red or pale red to brown solution (Fukushima et al., "Incompatibilities of Parenteral Injections," published by Fuji Print Co., Ltd., Press Dept., 1982, Section of "Adrenal Hormone Preparations", pp.384–395). Grubstein et al. (Grubstein, B. and Milano, E., Drug Development and Industrial Pharmacy, 18, pp.1549–1566, 1992) reported an issue of stabilization of epinephrine formulated in local anesthetics.

The aforementioned "Xylocaine® Cartridge for Dental Use" (Fujisawa Pharmaceutical Co., Ltd.) containing epinephrine is formulated with sodium pyrosulfite as an anti-oxidant in a content ratio of 0.6 mg per ml to prevent the oxidation of epinephrine. There are also known a formulation comprising a dental local anesthetic composition containing lidocaine and epinephrine added with dried sodium sulfite as an anti-oxidant ("Xylestesin A," Hakusui Trading, Co., Ltd.), and a formulation comprising a dental local anesthetic composition containing lidocaine and norepinephrine (0.04 mg per 1 ml) added with dried sodium sulfite as an anti-oxidant ("Xylestesin," Hakusui Trading Co., Ltd.).

The inventors of the present invention conducted studies to provide a composition for local anesthesia suitable for tooth extraction or the like by decreasing a content of a catecholamine based on lidocaine. In the course of the studies, they found that the oxidative degradation of a catecholamine was remarkably accelerated by lowering the content of a catecholamine such as epinephrine. They also found that catecholamines are extremely unstable to oxidation in a composition for anesthesia containing a catecholamine in an amount of about 1/200,000 (W/V: g/ml, 0.005 mg as a free base per 1 ml), and that it is quite difficult to store the composition stably by using sodium pyrosulfite or dried sodium sulfite which is conventionally used as an antioxidant. These problems have not been suggested or taught to date in the field of the art.

Grubstein et al. as mentioned above (Grubstein, B. and Milano, E., Drug Development and Industrial Pharmacy, 18, pp.1549–1566, 1992) discloses the results of stabilization of epinephrine in formulations containing pyrosulfite and citric acid in combination (Table1, Code D). However, these results are not unexpectedly superior to the results obtained by using pyrosulfite alone. In addition, the results neither suggest nor teach stabilizing effect of citric acid for epinephrine. Furthermore, these results were obtained by formulations containing epinephrine in an amount of 1/80,000 (W/V), and do not teach the fact that the stability of epinephrine is markedly reduced with decreasing amount of epinephrine.

A package insert (published in January, 1994) of Xylocaine® (lidocaine HCl injection, USP), an agent for dental local anesthesia sold by Astra USA, Inc., Westborough, Mass., USA, describes in Table 1 an aqueous solution containing lidocaine (2%) and epinephrine at a concentration of 1/100,000 or 1/50,000 (g/ml) together with citric acid (0.2 mg/ml). However, the package insert neither suggests nor teaches an action of citric acid contained in the aqueous solution. Furthermore, the agent for local anesthesia also contains epinephrine at a high concentration, and therefore, the product does not teach the fact that the stability of epinephrine is markedly reduced with decreasing amount of epinephrine.

DISCLOSURE OF THE INVENTION

An object of the present invention is to provide a composition for local anesthesia which provides solutions to the problems mentioned above. More specifically, the object of the present invention is to provide a composition for local anesthesia which contains an about several-fold reduced amount of a catecholamine compared to conventional formulations, and has excellent storage stability based on prevention of the oxidative degradation of the catecholamine.

Another object of the present invention is to provide a composition for local anesthesia which has a duration suitable for a short-time dental operation such as tooth extraction and has excellent storage stability.

A further object of the present invention is to provide a stabilizer for a catecholamine which can prevent remarkable oxidative degradation of catecholamines which is caused when a content of a catecholamine based on lidocaine is decreased several times as compared to conventional formulations.

The inventors of the present invention conducted various researches to achieve the foregoing objects, and as a result, they found that a compound selected from the group consisting of hydroxycarboxylic acids and amino acids can remarkably stabilizes a catecholamine in a composition comprising a catecholamine in an amount of about 1/200, 000 (g/ml) (weight as a free base) based on a volume of the composition, and that a composition for local anesthesia which comprises (A) lidocaine hydrochloride, (B) a catecholamine in an amount of about 1/200,000 (g/ml) (weight as a free base), and (C) one or more compounds selected from the group consisting of hydroxycarboxylic acids and amino acids, has a duration extremely suitable for short-time dental operations such as tooth extraction and excellent storage stability. The present invention was achieved on the basis of these findings.

The present invention thus provides a composition for local anesthesia which comprises: (A) lidocaine, (B) a catecholamine in an amount of about 1/80,000–1/300,000 (g/ml) (weight as a free base) based on a volume of the composition, and (C) one or more amino acids. According to preferred embodiments of the invention, there are provided the aforementioned composition which contains about 1/200,000 (g/ml) of epinephrine; the aforementioned composition which has excellent storage stability; the aforementioned composition which is used for a shot-time dental operation; the aforementioned composition wherein the amino acid acts as a stabilizer of the catecholamine; the aforementioned composition wherein the amino acid is an α-amino acid; the aforementioned composition wherein the amino acid is an L-amino acid; and the aforementioned composition wherein one or more amino acids are selected from the group consisting of glycine, glutamic acid, aspartic acid, phenylalanine, and L-glutamic acid-L-lysine.

According to another aspect of the present invention, there is provided a composition for local anesthesia which comprises: (A) lidocaine, (B) a catecholamine in an amount of about 1/120,000–1/300,000 (g/ml) (weight as a free base) based on a volume of the composition, and (C) one or more hydroxycarboxylic acids. According to preferred embodiments of this invention, there are provided the aforementioned composition which contains about 1/200,000 (g/ml) of epinephrine; the aforementioned composition which has excellent storage stability; the aforementioned composition which is used for a short-time dental operation; the aforementioned composition wherein the hydroxycarboxylic acid acts as a stabilizer of the catecholamine; the aforementioned composition wherein the hydroxycarboxylic acid is selected from the group consisting of lactic acid, glycolic acid, and citric acid; and the aforementioned composition wherein the hydroxycarboxylic acid is selected from the group consisting of lactic acid and glycolic acid.

According to further aspect of the present invention, there are provided a stabilizer selected from amino acids which is used for a composition for local anesthesia comprising lidocaine together with a catecholamine in an amount of about 1/80,000–1/300,000 (g/ml) (weight as a free base) based on a volume of the composition, and a stabilizer selected from hydroxycarboxylic acids which is used for a composition for local anesthesia comprising lidocaine together with a catecholamine in an amount of about 1/120, 000–1/300,000 (g/ml) (weight as a free base) based on a volume of the composition. According to preferred embodiments of these inventions, there are provided aforementioned stabilizer wherein said composition comprises about 1/200,000 (g/ml) of epinephrine; the aforementioned stabilizer which has an effect to suppress the oxidative degradation of the catecholamine; the aforementioned stabilizer wherein the hydroxycarboxylic acids are selected from the group consisting of lactic acid, glycolic acid, and citric acid; the aforementioned stabilizer wherein the amino acids are α-amino acids; the aforementioned stabilizer wherein the amino acids are L-amino acids; and the aforementioned stabilizer wherein the amino acids are selected from the group consisting of glycine, glutamic acid, aspartic acid, phenylalanine, and L-glutamic acid-L-lysine.

Best Mode for Carrying Out the Invention

The composition of the present invention is characterized in that said composition contains lidocaine and a catecholamine in a specific range of concentration, and further contains one or more hydroxycarboxylic acids or amino acids as being compounds stabilizing the catecholamine. Lidocaine is ordinarily used as a substance for an active ingredient of a local anesthetic agent, and can be obtained easily. As the lidocaine, for example, salts such as lidocaine hydrochloride are preferably used. A content of lidocaine in the composition of the present invention is, for example, 10–30 mg, preferably about 20 mg as the weight of lidocaine hydrochloride per 1 ml of the composition.

As the catecholamines, for example, epinephrine, norepinephrine, phenylephrine or other may be used. These compounds as free bases may be used, or alternatively, salts such as hydrochlorides and tartrates may also be used. As the salts, for example, epinephrine hydrochloride, epinephrine hydrogen tartrate, norepinephrine hydrochloride, norepinephrine hydrogen tartrate or other may preferably used. Among them, epinephrine hydrochloride or epinephrine hydrogen tartrate is most preferably used.

A content of the aforementioned catecholamine in the composition of the present invention is in a ratio ranging from 1/80,000–1/300,000, preferably less than 1/80,000 and equal to or more than 1/300,000 as a weight of a free base (g) based on a volume of the composition (ml). More specifically, when one or more amino acids are used as a compound acting on stabilization, 1/80,000–1/300,000, preferably less than 1/80,000 and equal to or more than 1/300,000 of a catecholamine as a weight of a free base (g) based on a volume of the composition (ml) may be used. When a hydroxycarboxylic acid is used as a compound acting on stabilization, 1/120,000–1/300,000, preferably less than 1/18,000 and equal to or more than 1/300,000 of a catecholamine based on a volume of the composition (ml) may be used.

The amount of a catecholamine contained in conventionally used dental local anesthetics, which contain lidocaine as an active ingredient, is 0.0125 mg (1/80,000 g/ml) for epinephrine, and 0.04 mg (1/25,000 g/ml) for norepinephrine per 1 ml of the composition containing 20 mg of lidocaine hydrochloride. In the composition of the present invention, a content of a catecholamine based on lidocaine is decreased compared to conventional formulations, and as a consequence, the composition has a duration of local anesthetic action extremely suitable for dental local anesthesia, in particular, local anesthesia for minor operations such as tooth extraction. When the composition of the present invention is formulated with epinephrine, an amount of, for example, 1/150,000–1/300,000 (g/ml), preferably 1/170,000–1/250,000 (g/ml), more preferably 1/180,000–1/220,000 (g/ml), and most preferably about 1/200,000 (g/ml) may be formulated. When norepinephrine is used, an amount of 1/80,000–1/150,000 (g/ml) may be formulated.

The hydroxycarboxylic acids are not particularly limited so long as they have one or more carboxyl groups together with one or more hydroxyl groups in their molecules. As the hydroxycarboxylic acid, for example, glycolic acid, gluconic acid, lactic acid, glyceric acid, malic acid, tartaric acid, citric acid, 2-hydroxy-n-butyric acid and the like can be used. Among them, glycolic acid, lactic acid, and citric acid are preferred; and glycolic acid or lactic acid may be more preferably used. Salts of hydroxycarboxylic acids may also be used. For example, sodium salts, potassium salts, calcium salts, magnesium salts and the like can be used.

The amino acids are not particularly limited so long as they are compounds having one or more carboxyl groups together with one or more amino groups in their molecules. For example, alanine, arginine, asparagine, aspartic acid, cysteine, glutamic acid, glutamine, glycine, histidine, isoleucine, leucine, lysine, methionine, phenylalanine, proline, serine, threonine, tryptophane, tyrosine, valine, 2-aminoadipic acid, 3-aminoadipic acid, β-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, 6-N-methyllysine, N-methylvaline, norvaline, norleucine, ornithine and the like can be used. Among them, α-amino acids may preferably be used, and glycine, glutamic acid, aspartic acid, and phenylalanine are most preferred amino acids.

As the amino acid, complex salts comprising two different amino acids may also be used. For example, glutamic acid-lysine, preferably L-glutamic acid-L-lysine (L-lysine L-glutamate or L-lysine L-glutamic acid salt), glutamic acid-arginine, preferably L-glutamic acid-L-arginine (L-arginine L-glutamate or L-arginine L-glutamic acid salt) and the like can be used. Compositions containing L-glutamic acid-L-lysine are particularly preferred embodiments according to the present invention.

As to the compounds having one or more asymmetric carbons among the hydroxycarboxylic acids and amino acids mentioned above, optical isomers in optically pure forms, any mixtures of the optical isomers, racemates, any mixtures of diastereoisomers or other may be used. One or more compounds selected from the group consisting of these hydroxycarboxylic acids and amino acids can be formulated in the composition of the present invention. Acid addition salts or base addition salts of the above compounds, for example, hydrochlorides, sulfates, p-toluenesulfonates, A sodium salts, potassium salts, ammonium salts and the like can also be used. Although it is not intended to be bound by any specific theory, the aforementioned hydroxycarboxylic acids and/or amino acids formulated in the composition of the present invention can prevent the oxidative degradation of a catecholamine which is accelerated in a diluted solution, and act as stabilizers for the catecholamine.

A content of the compound selected from the group consisting of hydroxycarboxylic acids and amino acids in a formulation is not particularly limited so far that the compound can act to stabilize a catecholamine. Generally, an amount of about 0.05 mg to 20 mg per 1 ml of the composition may be formulated. Stabilizing effect of the compound selected from the group consisting of hydroxycarboxylic acids and amino acids in the aforementioned composition can be readily determined by the method described in the examples set out below, and its content can be appropriately chosen depending on a type of the compound and a content of catecholamines.

The composition for local anesthesia of the present invention is a composition for injection in the form of an aqueous solution obtainable by dissolving in distilled water for injection the aforementioned components and one or more optional pharmaceutical additives which are available for those skilled in the art as additives to be formulated in compositions for topical injections. Generally, the composition is provided for clinical use after being filled in ampoules, vials, cartridges or the like under sterile condition. As the pharmaceutical additives, for example, isotonicities to adjust osmotic pressure ratio to about 0.8–1.3, preferably about 1.0, e.g., sodium chloride; pH modifiers to adjust pH to a range of about 3.0–6.5, preferably 3.3–5.0, e.g., hydrochloric acid or sodium hydroxide; antiseptics, e.g., methyl p-hydroxybenzoate, and other may be used.

The composition for local anesthesia of the present invention can be suitably used for minor operations in oral surgery and dental treatment, preferably for operations which can be completed in several to ten minutes such as tooth extraction in dental treatment. However, applicable therapies are not limited to the uses in oral surgery and dental treatment, and the composition can be used for surgical local anesthesia such as for skin incision. The composition of the present invention can be prepared by a method well-known to those skilled in the art. Specific examples of the method for producing the composition of the present invention are detailed in the following examples. However, methods for preparing the composition of the present invention are not limited to those described in the examples, and in addition, appropriate alterations and modifications can be added to these methods.

EXAMPLES

The present invention will be explained more specifically by referring to the following examples. However, the scope of the present invention is not limited to these examples.

Example 1

Lidocaine (17.3 g) was dissolved in hydrochloric acid (6 ml), and the solution was added with distilled water for injection (about 20 ml) to prepare Solution A. Lactic acid (1.0 ml) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 2

Lidocaine (17.3 g) was dissolved in hydrochloric acid (6 ml), and the solution was added with distilled water for injection (about 20 ml) to prepare Solution A. Sodium glycolate (10.0 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 3

Lidocaine (17.3 g) was dissolved in hydrochloric acid (6 ml), and the solution was added with distilled water for injection (about 20 ml) to prepare Solution A. Sodium citrate (0.1 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 4

Lidocaine (17.3 g) was dissolved in hydrochloric acid (6 ml), and the solution was added with distilled water for injection (about 20 ml) to prepare Solution A. Glycine (10.0 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 5

Lidocaine (17.3 g) was dissolved in hydrochloric acid (6 ml), and the solution was added with distilled water for injection (about 20 ml) to prepare Solution A. Sodium glutamate (10.0 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 6

Lidocaine (17.3 g) was dissolved in hydrochloric acid (6 ml), and the solution was added with distilled water for injection (about 20 ml) to prepare Solution A. Aspartic acid (4.0 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to 1,000 ml to prepare a composition for local anesthesia of the present invention.

Example 7

Lidocaine (17.3 g) was dissolved in hydrochloric acid (6 ml), and the solution was added with distilled water for injection (about 20 ml) to prepare Solution A. Phenylalanine (10.0 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 8

Lidocaine (17.3 g) was dissolved in hydrochloric acid (6 ml), and the solution was added with distilled water for injection (about 20 ml) to prepare Solution A. L-Glutamic acid-L-lysine (20.0 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 9

Lidocaine (17.3 g) was dissolved in hydrochloric acid (6 ml), and the solution was added with distilled water for injection (about 20 ml) to prepare Solution A. L-Glutamic acid-L-lysine (10.0 g), anhydrous sodium sulfite (0.6 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare the composition for local anesthesia of the present invention.

Example 10 (Comparative composition)

Lidocaine (17.3 g) was dissolved in hydrochloric acid (6 ml), and the solution was added with distilled water for injection (about 20 ml) to prepare Solution A. Sodium chloride (2.0 g) was dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare a composition for local anesthesia for comparison.

Example 11 (Comparative composition)

Lidocaine (17.3 g) was dissolved in hydrochloric acid (6 ml), and the solution was added with distilled water for injection (about 20 ml) to prepare Solution A. Sodium pyrosulfite (0.6 g) and sodium chloride (2.0 g) were dissolved in distilled water for injection (about 800 ml), and the solution was added with Solution A and mixed. After this solution was adjusted to pH 4.0 by adding a sufficient quantity of hydrochloric acid, epinephrine hydrogen tartrate (9.0 mg) was dissolved in the resulting solution, and then the solution was added with distilled water for injection up to the total volume of 1,000 ml to prepare a composition for local anesthesia for comparison.

Example 12 (Test example)

Each of the compositions of Examples 1–9 and the comparative compositions of Examples 10 and 11 (each 5 ml) was filled in a vial, and alterations in epinephrine content (residual amounts) were measured after storage for 7 days and 21 days at 40° C. The results are shown in Table 1.

TABLE 1

| Composition | Epinephrine content (%) | | | Appearance |
| --- | --- | --- | --- | --- |
|  | 0th day | 7th day | 21st day | 21st day |
| Example 1 | 100 | 100 | 97 | Colorless and clear |
| Example 2 | 100 | 100 | 98 | Colorless and clear |
| Example 3 | 100 | 99 | 99 | Colorless and clear |
| Example 4 | 100 | 98 | 95 | Colorless and clear |
| Example 5 | 100 | 99 | 96 | Colorless and clear |
| Example 6 | 100 | 100 | 100 | Colorless and clear |
| Example 7 | 100 | 99 | 97 | Colorless and clear |
| Example 8 | 100 | 100 | 99 | Colorless and clear |
| Example 9 | 100 | 100 | 100 | Colorless and clear |
| Example 10 | 100 | 71 | 48 | Colored |
| Example 11 | 100 | 78 | 62 | Colored |

Industrial Applicability

The compositions for local anesthesia of the present invention are useful since the composition have a duration suitable for short-time dental operations such as tooth extraction and excellent storage stability.

What is claimed is:

1. A composition for local anesthesia which comprises (A) lidocaine, (B) epinephrine in an amount of about 1/150,000–1/300,000 weight as a free base based on a volume of the composition, and (C) one or more amino acids.

2. The composition according to claim 1 which contains about 1/2000,000 g/ml of epinephrine based on the volume of the composition.

3. The composition according to claims 1 or 2 wherein said one or more amino acids is selected from the group consisting of glycine, glutamic acid, aspartic acid, phenylalanine, and glutamyllysine.

4. The composition according to claim 2 wherein said one or more amino acids is L-glutamic acid-L-lysine.

5. A composition for local anesthesia which comprises (A) lidocaine, (B) a catecholamine in an amount of about 1/120,000–1/300,000 g/ml weight as a free base based on a volume of the composition, and (C) one or more hydroxycarboxylic acids.

6. The composition according to claim 5 wherein said catecholamine is epinephrine.

7. The composition according to claim 6 which contains about 1/200,000 g/ml of epinephrine based on the volume of the composition.

8. The composition according to claims 5, 6 or 7 wherein said hydroxycarboxylic acid is selected from the group consisting of lactic acid, glycolic acid, and citric acid.

9. The composition according to claims 5, 6 or 7 wherein the hydroxycarboxylic acid is selected from the group consisting of lactic acid and glycolic acid.

10. A stabilizer which is formulated in a composition for local anesthesia comprising lidocaine, and a catecholamine in an amount of about 1/120,000–1/300,000 g/ml weight corresponding to a free base based on a volume of the composition and wherein said stabilizer is selected from the group consisting of hydroxycarboxylic acids and amino acids.

11. The stabilizer according to claim 10 which is formulated in a composition comprising about 1/200,000 g/ml of epinephrine based on the volume of the composition and wherein said stabilizer is selected from the group consisting of hydroxycarboxylic acids and amino acids.

12. The stabilizer according to claim 10 or 11 wherein said stabilizer is L-glutamic acid-L-lysine.

13. A composition for local anesthesia which comprises (A) lidocaine, (B) norepinephrine in an amount of about 1/80,000–1/300,000 g/ml weight as a free base based on a volume of the composition, and (C) one or more amino acids.

14. The composition according to claim 13 wherein said one or more amino acids is selected from the group consisting of glycine, glutamic acid, aspartic acid, phenylalanine, and glutamyllysine.

15. The composition according to claim 14 wherein said one or more amino acids is L-glutamic acid-L-lysine.

* * * * *